Figure 1:

United States Patent [19]
Malmberg et al.

[11] Patent Number: 4,751,348
[45] Date of Patent: Jun. 14, 1988

[54] NICOTIANA PLANTS WITH BOTH ALTERED POLYAMINE LEVELS AND FLOWER STRUCTURES AND METHOD FOR OBTAINING THESE PLANTS

[75] Inventors: Russell L. Malmberg, Huntington Station; Jean McIndoo, Norwich, both of N.Y.

[73] Assignee: Cold Spring Harbor Laboratory, Cold Spring, N.Y.

[21] Appl. No.: 511,346

[22] Filed: Jul. 16, 1983

[51] Int. Cl.[4] .................... C12N 15/00; C12N 5/00
[52] U.S. Cl. .................................. 800/1; 435/172.2; 435/240.49; 435/240.54; 47/58
[58] Field of Search ............... 435/240, 241, 172.1, 435/240.49, 240.54; 47/58; 800/1; 935/94, 67

[56] References Cited

PUBLICATIONS

Morris et al., (1977), "Inhibition of the Synthesis of Polyamines and DNA in Activated Lymphocytes by a Combination of α-MO and MGBG, "*Cancer Research*, vol. 37, pp. 3169-3172.

Weber et al., (1980), "Quantitative Measurement of the Ability of Different Mutagens to Induce an Inherited Change in Phenotype to Allow Maltose Utilization in Suspension Cultures of *Glycine max* (L.) Merr.", *Genetics*, vol. 96, pp. 213-222.

Chaleff, (1983), "Isolation of Agronomically Useful Mutants from Plant Cell Cultures", *Science, vol.* 219, pp. 676-682.

Jendrisak et al., (1976), "Wheat Germ DNA-Dependent RNA Polymerase II: Purification and Properties", in *RNA Polymerase*, Cold Spring Harbor Laboratory, Losick and Chamberlin, eds., pp. 779-791.

Yao-Red Dai, et al., "Promotion by Gibberellic Acid of Polyamine Biosynthesis in Internodes of Light-Grown Dwarf Peas", Plant Physiol., (1982), 69, 103-105.

Russell L. Malmberg, "Biochemical, Cellular and Developmental Characterization of a Temperature-Sensitive Mutant of Nicotiana Tabacum and Its Second Site Revertant", Cell, vol. 22, 603-609.

Yao-Ren Dai, et al., "Simultaneous Phytochrome-Controlled Promotion and Inhibition of Arginine Decarboxylase Activity in Buds and Epicotyls of Etiolated Peas", Plant Physiol., (1981), 67, 266-269.

Akiva Apelbaum, et al., "Polyamines Inhibit Biosynthesis of Elthylene in Higher Plant Tissue and Fruit Protoplasts", Plant Physiol, (1981), 68, 453-456.

Michael J. Montague, et al., "Polyamine Metabolism in Embryogenic Cells of Daucus Carota", Plant Physiol., (1978), 62, 430-433.

Yair M. Heimer, et al., "Characterization of Ornithine Decarboxylase of Tobacco Cells and Tomato Ovaries", Biochem. J., (1982), 201, 373-376.

Russell L. Malmberg, "Temperature Sensitive Variants of Nicotiana Tabacum Isolated from Somatic Cell Culture", Genetics, (1979), 92: 215-221.

J. E. Smart, et al., "Adenovirus Type 2 Early Proteins: Assignment of the Early Region 1A Proteins Synthesized in Vivo and in Vitro to Specific mRNAs", Virology, (1981), 112, 703-713.

Pierre S. Mamont, et al., "Effects of Ornithine Decarboxylase Inhibitors on Cultured Cells", 1978, Elsevier/North/Holland Biomedical Press, Enzyme-Activated Irreversible Inhibitors, N. Seiler, et al., eds.

Toshio Murashige, et al., "A Revised Medium for Rapid Growth and Bio Assays with Tobacco Tissue Cultures", Physiologia Plantarum, vol. 15, 473, 1962.

Hecter E. Flores, et al., "Analysis of Polyamines in Higher Plants by High Performance Liquid Chromatography", Plant Physiol., (1982), 69, 701-706.

*Primary Examiner*—Thomas G. Wiseman
*Assistant Examiner*—Stephanie Seidman
*Attorney, Agent, or Firm*—Felfe & Lynch

[57] ABSTRACT

Plant cell lines with altered flower structures, and altered plant male and/or female sterility/fertility, and altered polyamine synthesis have been isolated using a UV mutagenizing light, polyamine synthesis inhibitors, and growth in the dark. Some of these cell lines are resistant to MGBG and exhibit elevated polyamine synthesis. Regenerated plants with unusual flowers are thus possible as are crop and flower plants with unusual flowers, and/or altered fertility capability by the method of the invention. These plant lines are also useful as research tools.

19 Claims, 2 Drawing Sheets

NICOTIANA PLANTS WITH BOTH ALTERED POLYAMINE LEVELS AND FLOWER STRUCTURES AND METHOD FOR OBTAINING THESE PLANTS

This invention was made with Government support under grant PCM 8203213 awarded by the National Science Foundation. The U.S. Government has certain rights in this invention.

Plant research seeks variants and mutants which will breed true for specific characteristics such as rapid growth, altered or new floral types, altered fertility or sterility. It would be useful to be able to develop those variants or mutants from plant cell cultures which would regenerate into whole plants. Male or female sterile plants which do not produce seed are very useful for flower and crop purposes since once a hardy and/or useful and/or beautiful and/or productive line with such characteristics is found, cross-breeding by others or by nature, in or out of the field is curtailed. A male sterile plant reduces the amount of work in plant breeding by elimination of the need for hand pollution and/or emasculation. The plant cell lines of the present invention possess altered flower structures with concommitant alterations in anther and ovule structures with changes in male and/or female characteristics. Also elevated levels of polyamines in these lines suggest a possible link between the two effects.

Polyamines have been implicated as being possible important growth promoters in plant biochemistry [Flores et al, *Plant Physiol,* 69: 701 (1982), Dai et al *Plant Physiol,* 69: 103 (1982)]. Mammalian systems seem to require continuous polyamine synthesis to maintain maximum rates of cell proliferation especially in rapidly growing cells. Depletion of polyamines can lead to a decrease in DNA synthesis. (Mamont et al in *Enzym-activated Inreversible Inhibitors* ed by N. Seiler, M. J. Jung and J. Koch-Wester, 1978, Elsevier/North-Holland Biomedical Press). Certainly such cell lines are useful as research tools to investigate polyamines and their relation to growth in living tissues. We speculate that plants with elevated polyamine synthesis could have potential use as a source of crops and/or ornamental or flowering plants which regenerate faster from cell culture or grow faster in the field.

The method of the present invention involves irradiating plant cell lines in tissue culture, followed by alternating dark and light growth phases, then plant selection steps with regeneration of whole plants which have altered flower structures with accompanying changes in male or female fertility characteristics and/or elevated polyamine levels.

A detailed description of the method as applied to *Nicotiana tabacum cv Xanthi* cells in culture follows. This is for example purposes. It will be obvious to those skilled in the art that the method as applied to liquid suspension cultures could be used with other tissue systems such as callus cultures, protoplast cultures, embryo cultures, seed selections i.e. other plant cell, tissue, and organ culture systems. Indeed other crop and flower plants as well will obviously be useful as subject plant material specimen providers under the present invention. Therefore, the invention is useful for all types of crop and flower plant specimens and cultures to yield useful variants and hybrids. It is also obvious to those skilled in the art to use the variety of flower and/or crop plant specimens described above, in conjunction with other polyamine synthesis inhibitors, such as alpha-methylornithine or defluoromethylornithine as well as Methylglyoxal-bis(guanylhydrazone) (MGBG) to produce polyamine synthetic variants or mutants. In addition, other mutagens may be used, or mutagens may be deleted from the method.

The following example as applied to *Nicotiana tabacum cv Xanthi* in the presence of MGBG, is for illustrative purposes only and is not meant to limit the invention.

Example of method:

Liquid Suspension culture cells of *Nicotiana tabacum cv Xanthi* are grown in Murashige-Skoog medium [Murashige et al *Physiologia Plantarum,* 15 473 (1962)]. See Table 1 below.

TABLE 1

MEDIUM FOR TABACCO TISSUE CULTURES
Composition of plant growth medium. pH adjusted to 5.7–5.8 with HCl, KOH, or NaOH

A. Mineral salts

| Major elements | | | | Minor elements | | |
|---|---|---|---|---|---|---|
| Salts | mg/l. | mM | | Salts | mg/l | Micromolar |
| $NH_4NO_3$ | 1650 | N | 41.2 | $H_3BO_3$ | 6.2 | 100 |
| $KNO_3$ | 1900 | | 18.8 | $MnSO_{24}.4H_2O$. | 22.3 | 100 |
| $CaCl_2.2H_2O$ | 440 | | 3.0 | $ZnSO_4.4H_2O$. | 8.6 | 30 |
| $MgSO_4.7H_2O$ | 370 | | 1.5 | KI | 0.83 | 5.0 |
| $KH_2PO_4$ | 170 | | 1.25 | $Na_2MoO_4.2H_2O$ | 0.25 | 1.0 |
| $Na_2$—EDTA | 37.3[1] | Na | 0.20 | $CuSO_4.5H_2O$ | 0.025 | 0.1 |
| $FeSO_4.7H_2O$ | 27.3[1] | Fe | 0.10 | $CoCl_2.6H_2O$ | 0.025 | 0.1 |

B. Organic constituents

| | | | | |
|---|---|---|---|---|
| Sucrose | 30 g/l. | | Agar | 10 g/l. |
| Indoleacetic acid | 0–3 mg/l. | | myo-Inositol | 1 g/l. |
| Kinetin | 0–0.3 mg/l. | | Nicotinic acid | 1 mg/l. |
| Dimethyl allyl aminopurine | 0–10 mg/l | | Pyridoxin HCl | 1 mg/l. |
| | | | Thiamin HCl | 10 mg/l. |
| 2,4-dichloro-phenoxyacetic acid | 0–1 mg/l | | | |

[1] 5 ml/l of a stock solution containing 5.57 g $FeSO_4.7H_2O$ and 7.45 g $Na_2$—EDTA per liter of $H_2O$.

The plant specimens are then exposed to ultraviolet light three inches from the specimen plant for twenty minutes. The plant cells are exposed long enough to result in approximately 30% death as assayed by 0.1% bromphenol blue staining 24 hours after irradiation. The UV light used should result in some mutagenesis. Other mutagens that might work are (1) spontaneous, (2) chemical, (3) insertional or transposon or (4) ionizing irradiation.

The cells are then subcultured into fresh Murashige-Skoog medium wherein the ammonium and potassium nitrates are replaced by 30 mM L-glutamine. The cells are then incubated in the dark for at least one generation.

The cells are then plated onto petri plates containing the same medium in agar without potassium or ammonium nitrates but containing 30 mM L-glutamine and an inhibitor of polyamine synthesis, such as 1–10 mM MGBG (which is insoluble in the ordinary medium containing nitrate). The preferred concentration of MGBG is 10 mM. Other polyamine synthesis inhibitors can be used e.g. specific inhibitors of enzymes involved in polyamine synthesis such as ornithine decarboxylase (ODC) or S-adenosylmethionine decarboxylase (SAM-DC). MGBG is an inhibitor of SAM-DC. Alpha-methylornithine and difluoromethylornithine (DFMO) inhibit ODC.

The plating is done by taking the liquid cultures after the dark incubation period, letting them settle for 15 minutes in a graduated centrifuge, removing the supernatant and adding lukewarm agar medium in a volume equal to that of the cells. This lukewarm-soft agar-cell mixture is pipetted onto the petri plates in the range of about 5-20 ml/plate. The plates are wrapped in parafilm and incubated in the dark at about 26° C.

Two-four months later colonies will appear on the plates. These MGBG-resistant colonies are grown on medium without MGBG and then a liquid suspension culture is formed from each of these colonies. This culture is tested for stable resistance to MGBG. Finally, plants can be regenerated from such stably resistant cultures.

One such resistant culture isolated by the above method is Mgr3, and it regenerated into a plant at about the same rate as the parent cell line under standard regeneration conditions [Malmberg, R. L., Genetics, 92, 215-221 (1979)] (See FIG. 1). FIG. 1 is a color photograph of regenerated Mgr3. Mgr3 is a dark green plant with very short inter-nodes. Cell cultures derived from Mgr3 plant leaves ae fully resistant to MGBG.

Mgr3 plants produce flowers with several unusual effects. The flowers initially appear normal, but then the stigma grows past the corolla until it exerts perhaps 5 mm; then the stigma turns black. The anthers appear normal initially, but never contain viable pollen, and they die about the time the stigma exerts. The ovary swells greatly, even though the plant has not been fertilized. Dissection of the ovary reveals that the hundreds of ovules normally found embedded in the placenta are converted into hundreds of anthers. Each ovary contained about 5 to 10 ovules that did not switch to the male meiotic structure. In some flowers that are dissected at an early stage, we see structures geographically and morphologically in between ovules and anthers. That is, between clusters of normal looking ovules and transformed ovules there are some elongated spheres and tubular structures that are apparent intermediates in the switching process. Together with the fact that the entire flower initially appears normal, these intermediates suggest that the early flower development is normal, but then at a specific late time, the ovules change their developmental pathway, turn into anthers, and cause the rest of development to be abnormal. Thus Mgr3 is female-sterile with abnormal flower structure. There seems to be a developmental alteration or switch in such plants.

Parent wild type anthers have a characteristic internal morphology revealed by dissection, consisting of four columns of cells in a lobed structure; we have observed similar structures in cross sections of the Mgr3 ovule-anthers. The transformed ovules never form a well defined sack, and never show pollen development, although the terminus is sometimes slightly enlarged with a dark green color. Thus Mgr3 is male-sterile, as well as female-sterile with abnormal flower structures.

Given that a female to male transition occurs, it is remarkable that the ovules do not change into equivalently advanced structures. The entire another is developmentally equivalent to the entire ovary; hence the switching process is female to male with concommitant return to a more basal level.

A temperature sensitive mutant ts4 was previously isolated by us, and a revertant of this mutant Rt1 showed flowers in which anthers were converted into petals. (Malmberg, Russell L. Cell 22: 603 (1980); Genetics 92: 215 (1979).

Analysis of the levels of polyamines in Mgr3 cultures and leaves are shown in Table 2 below, as compared to parent Wild-Type cultures and leaves using the method of Flores and Galston (Plant Physiology 69: 701 (1982)).

TABLE 2

Polyamine concentrations of Mgr3 and wild type-Parent Nicotiana Tabacum cv Xanthi

| Cell type | Concentration in nanomoles per gram (fresh weight) | | | |
| --- | --- | --- | --- | --- |
| | Agmatine | Putrescine | Spermidine | Spermine |
| Wild Culture | 348 | 480 | 427 | 49 |
| Wild Leaf | 218 | 406 | 431 | 23 |
| Mgr3 Culture | 272 | 182 | 520 | 50 |
| Mgr3 Leaf | 401 | 572 | 2035 | 159 |

In Mgr3 cultures, levels of putrescine are relatively low, while in the leaves of regenerated whole plants, the levels of spermidine and spermine are quite high. Putrescine to Spermidine ratio in wild type cultures as well as leaves is about 1:1 whereas in Mgr3 cultures and leaves it is about 1:3 or about 1:4.

The Rt1 cell line had altered polyamine synthesis as well but here levels were lower than found in the parent line. Thus the methods of present invention introduces new cell lines with new characteristics.

Figure 2:

Another MGBG resistant cell line (Mgr12) has been isolated by the method as described above, and regenerated into a whole flowering plant (see FIG. 2). FIG. 2 is a color photograph of regenerated Mgr12. This flower is closer to normal morphology than in the Mgr3 line. Mgr12 is male sterile with no pollen formation from anther structures. Mgr12 is female fertile with normal ovary development and has been fertilized recently by wild type.

The MGBG effect may be on SAM-DC and/or some other facet of flower formation and/or polyamine synthesis. The existence of several independent mutants with altered polyamine synthesis and also altered floral development suggests there is a strong correlation between the two. Thus, polyamine synthesis may have interesting developmental regulation control effects. Also see: Montague, M., Kopperink, J. & Jaworski, E. Plant physiology 62: 430-433 (1978); Apelbaum, A., Burgoon, A., Anderson, J., Lieberman, M., Benarle, R. & Mattoo, A. Plant physiology 68: 453-456 (1981); Dai, Y. & Galston, A. Plant Physiology 67: 266-269 (1981); Dai, Y., Kaur-Sawhney, R. & Galston, A. Plant physiology 69: 103-105 (1982); Heimer, Y. & Mizrahi, Y. Biochem. J. 201: 373-376 (1982).

The wild type Nicotiana tabacum cv Xanthi can be induced to overproduce a polypeptide of about 30,000 MW, (absent in the wild type under normal growth conditions) when liquid suspension cultures are grown in the presence of sublethal amounts of MGBG, and/or amounts sufficient to double the generation time (e.g. 1-10 mM MGBG). This polypeptide is absent in Rt1 cell line but present in ts4 temperature sensitive mutant. Modified Murashige-Skoog medium with 30 mM L-glutamine replacing the nitrate salts is used (see Table I). Normal cells grown in this medium without MGBG have essentially the same polypeptide profile as wild type cells. Peptide maps are based on typtic digestion of $S^{35}$-methionine labelled polypeptides cut out of gels by the method of Smart et al [Virology 112 703 (1981)]. Tryptic peptides are analyzed on a high performance liquid chromatograph Spherisorb 10 ODS (C18) reverse phase column developed with a 0–62.5% ethanol gradient in 5% formic acid. ts4 also produces much of this 30,000 MW polypeptide and the typtic peptide maps of ts4 and the MGBG-induced cells are the same. This band of MW 30,000 mirrors the pattern of the ODC activities; the band is present in ts4 where ODC levels are low and absent in wild type and Rt1 where ODC levels are high.

The plants with altered polyamine synthesis are useful as research tools to study pathways of polyamine synthesis in plants and effects of MGBG on plant biochemistry. A further use is to study biochemical connections between polyamine synthesis and flower structures.

All cell lines discussed: Mgr3 and Mgr12, ts4, Rt1 are on deposit at Cold Spring Harbor Laboratory, P.O. Box 100 Bungtown Road, Cold Spring Harbor, N.Y. 11724. Mgr3 and Mgr12 are deposited on July 5, 1983 with the American Type Tissue Collection (ATCC), 12301 Parklawn Drive, Rockville, Md. 2052. Mgr3 has accession number and Mgr12 has accession number.

The process by which these plants are obtained could be valuable in leading to new types of flower morphologies, and specifically, new male sterile flowers. It is straightforward to envision application of these methodologies to both ornamental and food crop plants of economic value.

What is claimed is:

1. A method for producing a stable Nicotiana plant cell line from which sterile plants having altered flower structures and elevated amounts of spermine, spermidine and depressed putrescine: spermidine ratios may be regenerated which comprises:
   (a) irradiating a plant specimen in medium with UV light;
   (b) growing said irradiated plant specimen in the dark for a minimum of 1 generation time,
   (c) exposing said plant specimen to sublethal amounts of polyamine synthesis inhibitor selected from the group consisting of S-adenosyl methionine carboxylase and ornithine decarboxylase inhibitor for a minimum of about one generation time;
   (d) incubating the plant specimen from step (c) in modified medium,
   (e) selecting for a plant cell specimen capable of growth in the presence of polyamine synthesis inhibitor by means of growth in the presence of S-adenosyl methionine carboxylase or ornithine decarboxylase inhibitor wherein said plant cell line is capable of growth into male sterile, female sterile or male and female sterile plants with altered flower structures are selected from the group consisting of anthers which produce no pollen, ovaries which produce no seed and ovules which switch to anther structure.

2. Method of claim 1 wherein the irradiated wild type parent plant specimen is *Nicotiana tabacum cv Xanthi.*

3. Method of claim 1 wherein the irradiated plant specimens are selected from the group consisting of plant cells in culture, callus cultures, plant organ culture systems, embryo cultures, seeds, plant tissue cultures, protoplast cultures and mixtures thereof.

4. Method of claim 1 wherein the modified medium is modified Murashige-Skoog medium which contains L-glutamine instead of nitrate salts.

5. Method of claim 4 wherein the L-glutamine is approximately 30 mM.

6. Method of claim 1 wherein the polyamine synthesis inhibitor is selected from the group consisting of MGBG, alpha-methylornithine, difluoromethylornithine and mixtures thereof.

7. Method of claim 6 wherein the MGBG concentration in the range of approximately 1–10 mM.

8. Method of claim 6 wherein the MGBG concentration is 10 mM.

9. Method of claim 1 wherein UV light dose chosen produces approximately 30% dead cells.

10. Method of claim 9 wherein said dead cells are assayed 24 hrs. after irradiation by morbid staining with 0.1% bromphenol blue.

11. Method of claim 6 wherein the growth in MGBG in step (c) is for a minimum of about one generation time.

12. Stable, nicotiana mutant plant cell line capable of producing male or female sterile crop or ornamental plants with resultant altered flower development comprising
    growth in the presence of sublethal amount of polyamine synthesis inhibitors selected from the group of S-adenosyl-methionine decarboxylase and ornithine decarboxylase inhibitors;
    elevated intracellular levels of spermine and spermidine relative to the wild type;
    alteration of the putresine: spermidine ratio from a 1:1 range characteristic of the wild type to a 1:3–1:4 range; and
    growth into a sterile plant with altered flower development wherein the alteration is selected from the group consisting of anthers which produce no pollen, ovaries which produce no seed, ovule development switching to another development.

13. Cell line of claim 12 wherein the ornithine decarboxylase inhibitor is alpha-methylornithine or difluoromethylornithine.

14. Cell line of claim 12 derived from *Nicotiana tabacum cv Xanthi.*

15. Cell line of claim 12 selected from the group consisting of Mgr3 and Mgr12.

16. Cell line of claim 12 wherein the S-adenosylenethionine decarboxylase inhibitor is MGBG.

17. A plant cell line as produced by the method of claim 1.

18. Plant specimens regenerated from the plant cell line of claims 12, 14, 15, 16 or 17.

19. Plant specimens regenerated from the plant cell line of claim 17.

* * * * *

UNITED STATES PATENT AND TRADEMARK OFFICE
CERTIFICATE OF CORRECTION

PATENT NO. : 4,751,348
DATED : June 14, 1988
INVENTOR(S) : Malmberg et al.

Page 1 of 2

It is certified that error appears in the above-identified patent and that said Letters Patent is hereby corrected as shown below:

Col. 3, line 21: after "leaves" delete "ae" and insert -- are --.

Col. 3, line 60: after "entire" delete "another" and insert -- anther --.

Col. 5, line 20: delete "2052" and insert -- 20852 --.

Col. 5, line 21: after "Mgr 3 accession number" insert -- 40074 --; and after "Mgr 12 has accession number" insert -- 40075. These cell lines have been deposited with the ATCC under the Budapest Treaty. --.

Claim 4, Col.6, line 6 : after "salts" insert -- in steps (c) and (d) --.

UNITED STATES PATENT AND TRADEMARK OFFICE
CERTIFICATE OF CORRECTION

PATENT NO. : 4,751,348

DATED : June 14, 1988

INVENTOR(S) : Malmberg et al

It is certified that error appears in the above-identified patent and that said Letters Patent is hereby corrected as shown below:

Claim 16, Col. 6, lines 51-52; delete "S-adenosylenethionine" and insert -- S-adenosylmethionine --.

Signed and Sealed this

Eleventh Day of April, 1989

*Attest:*

DONALD J. QUIGG

*Attesting Officer*    *Commissioner of Patents and Trademarks*